Figure 1:
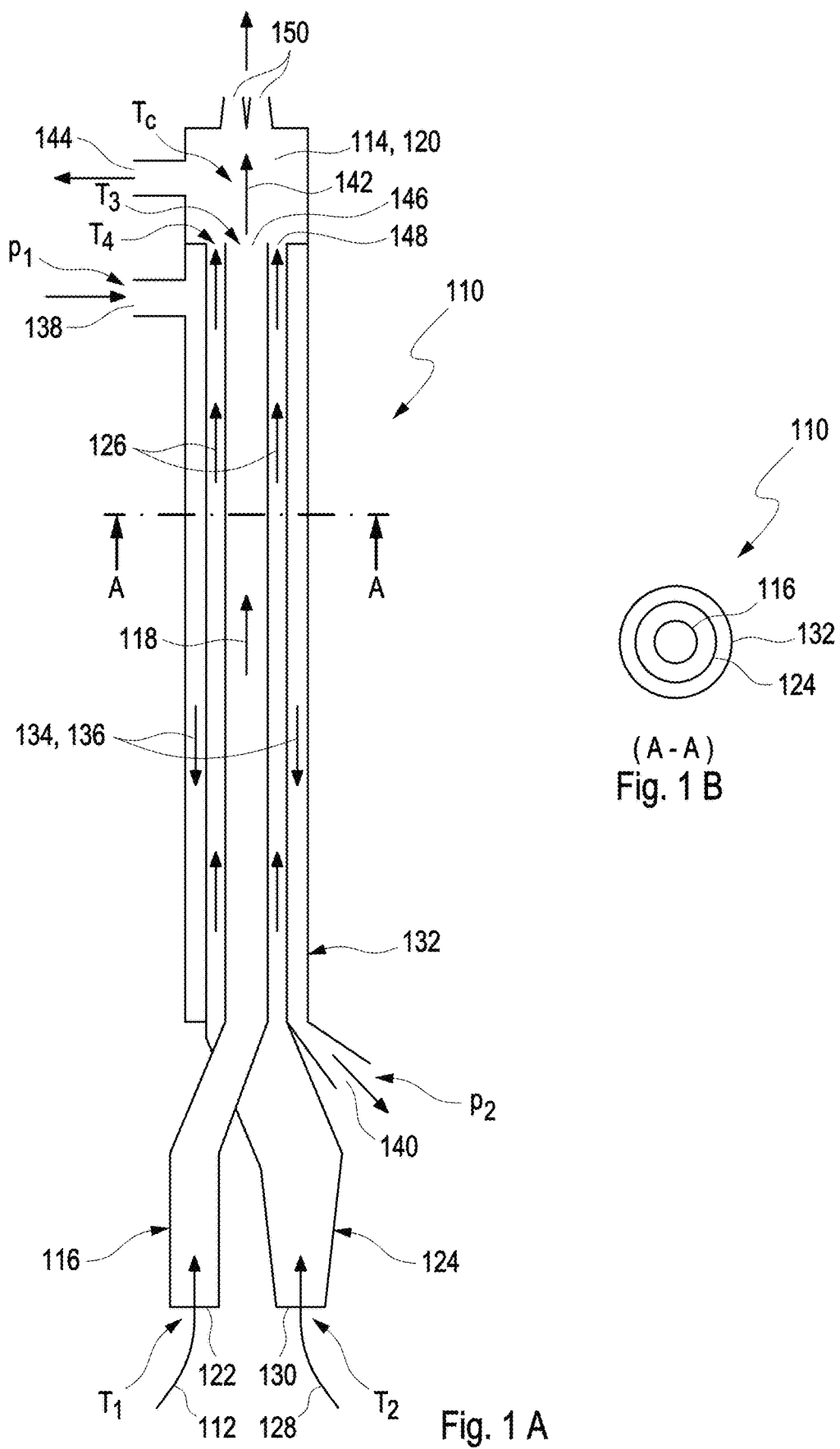

US011602608B2

(12) United States Patent
Pohlmann et al.

(10) Patent No.: US 11,602,608 B2
(45) Date of Patent: Mar. 14, 2023

(54) METHOD AND DEVICE FOR ADMINISTERING A HUMIDIFIED AEROSOL TO A PATIENT INTERFACE

(71) Applicant: Fraunhofer-Gesellschaft zur Förderung der angewandten Forschung e.V., Munich (DE)

(72) Inventors: Gerhard Pohlmann, Meerbeck (DE); Peter Iwatschenko, Neunkirchen (DE); Jelena Pankalla, Hannover (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 441 days.

(21) Appl. No.: 16/648,629

(22) PCT Filed: Sep. 17, 2018

(86) PCT No.: PCT/EP2018/075082
§ 371 (c)(1),
(2) Date: Mar. 18, 2020

(87) PCT Pub. No.: WO2019/053264
PCT Pub. Date: Mar. 21, 2019

(65) Prior Publication Data

US 2020/0215292 A1 Jul. 9, 2020

(30) Foreign Application Priority Data

Sep. 18, 2017 (EP) .................................... 17191624

(51) Int. Cl.

| | |
|---|---|
| *A61M 16/16* | (2006.01) |
| *A61M 16/08* | (2006.01) |
| *A61M 16/06* | (2006.01) |

(52) U.S. Cl.
CPC ........ *A61M 16/16* (2013.01); *A61M 16/0875* (2013.01); *A61M 16/0666* (2013.01);
(Continued)

(58) Field of Classification Search
CPC .............. A61M 16/16; A61M 16/0875; A61M 16/0666; A61M 16/161; A61M 16/162;
(Continued)

(56) References Cited

U.S. PATENT DOCUMENTS 5,031,612 A 7/1991 Clementi
2008/0072899 A1* 3/2008 Niland ............. A61M 16/1085 128/203.16

(Continued)

FOREIGN PATENT DOCUMENTS

GB 2 465 358 A 5/2010
WO WO 2008/030592 A2 3/2008

(Continued)

OTHER PUBLICATIONS

International Preliminary Report on Patentability, dated Mar. 24, 2020, in International Application No. PCT/EP2018/075082.
International Search Report & Written Opinion, dated Oct. 23, 2018, in International Application No. PCT/EP2018/075082.

(Continued)

*Primary Examiner* — Joseph D. Boecker
*Assistant Examiner* — Brian T Khong
(74) *Attorney, Agent, or Firm* — Knobbe, Martens, Olson & Bear LLP

(57) ABSTRACT

A method and device are used for administering a humidified aerosol to a patient interface by providing and guiding a first gas flow having a humidified aerosol, a second gas flow having humidified respiratory gases, and a liquid flow of a thermally balancing liquid, thermally balancing the first and second gas flow by parallel guiding the first and second (Continued)

gas flow such that the first and second gas flow are guided in a manner that they are at least partially surrounded by the liquid flow of the thermally balancing liquid, mixing the first and second gas flow to obtain enriched respiratory gases having the humidified aerosol, and administering the enriched respiratory gases to the patient interface. The method and the device avoid the administration of dry or re-dried powdered aerosols and unwanted accumulation of and blockage by powdered material. The device is useful in respiratory support of preterm infants.

17 Claims, 3 Drawing Sheets

(52) U.S. Cl.
CPC ................. *A61M 2202/064* (2013.01); *A61M 2205/3372* (2013.01); *A61M 2240/00* (2013.01)

(58) Field of Classification Search
CPC .............. A61M 16/164; A61M 16/165; A61M 16/167; A61M 16/168; A61M 16/1045; A61M 16/1075; A61M 16/108; A61M 16/1085; A61M 16/109; A61M 16/1095; A61M 16/12; A61M 16/14; A61M 11/02
See application file for complete search history.

(56) References Cited

U.S. PATENT DOCUMENTS

| | | | | |
|---|---|---|---|---|
| 2010/0006095 A1 | 1/2010 | Woodcock | | |
| 2013/0142782 A1* | 6/2013 | Rahmel | ................ | A61K 9/0075 424/130.1 |
| 2014/0216446 A1* | 8/2014 | Wruck | .................. | A61M 16/16 128/201.13 |
| 2015/0007817 A1* | 1/2015 | Longest | ............ | A61M 16/1095 128/203.14 |
| 2017/0000965 A1* | 1/2017 | Cortez, Jr. | ........ | A61M 16/0672 |
| 2020/0139074 A1* | 5/2020 | Longest, Jr. | ...... | A61M 16/1085 |

FOREIGN PATENT DOCUMENTS

| | | |
|---|---|---|
| WO | WO 2012/025496 A1 | 3/2012 |
| WO | WO 2014/095858 A1 | 6/2014 |
| WO | WO 2015/132172 A1 | 9/2015 |

OTHER PUBLICATIONS

Pohlmann, G., et al., A Novel Continuous Powder Aerosolizer (CPA) for Inhalative Administration of Highly concentrated Recombinant Surfactant Protein-C (rSP-C) Surfactant to Preterm Neonates, Journal Of Aerosol Medicine And Pulmonary Drug Delivery, vol. 26, No. 6, pp. 370-379, 2013.

* cited by examiner

METHOD AND DEVICE FOR ADMINISTERING A HUMIDIFIED AEROSOL TO A PATIENT INTERFACE

PRIORITY AND CROSS REFERENCE TO RELATED APPLICATIONS

This application is the U.S. National Phase Application under 35 U.S.C. § 371 of International Application No. PCT/EP2018/075082, filed Sep. 17, 2018, designating the U.S. and published in English as WO 2019/053264 A1 on Mar. 21, 2019, which claims the benefit of European Application No. EP 17191624.0, filed Sep. 18, 2017.

FIELD OF THE INVENTION

The present invention relates to a method, a device and a use thereof for administering a humidified aerosol to a patient interface. More particular, the method and the device may be designed for providing enriched respiratory gases comprising the humidified aerosol to the patient interface.

RELATED ART

As for example described in WO 2015/132172 A1, a dry material, also denotable as "aerosolizable material", which comprises particles of a powdered substance, preferably a pharmaceutical preparation, is treated in an aerosolization device by a compressed carrier gas in order to entrain the particles into a gas stream which are hereby converted to the desired aerosol, also denominated as "powdered aerosol". In this state, the particles of the dry material are distributed across the entire volume of the carrier gas, preferably in a uniform and finely dispersed form.

Such kinds of devices are, typically, used for inhalative administration of pharmaceutical preparations to patients which are breathing normally, to mechanically ventilated patients or to patients who are under ventilatory support. For normally breathing patients, typical examples include handheld dry powder inhalers or metered dose inhalers. For patients who are subject to mechanical ventilation or ventilatory support, a ventilatory circuit is used. For this purpose, a patient interface is integrated into, or attached to, the ventilatory circuit, wherein the ventilatory circuit, in general, comprises a ventilator and tubes adapted for guiding gases from the ventilator to a patient interface and back. In particular, a suitable mouthpiece, a breathing mask, a nasal cannula or a tracheal cannula are part of the patient interface or attachable thereto. A continuous inhalative administration of liquid aerosols can nowadays be considered as standard therapy for ventilated patients in intensive care units.

Pharmaceutical preparations can be administered in form of an inhalable dry powder by using dry powder inhalers, as for example disclosed in from US 2010/006095 A1. However, an inhalation of powdered aerosols, in particular of hygroscopic powdered aerosols, may result in intolerance, incompatibility or other adverse reactions, especially in the oral mucosa. As described in G. Pohlmann et al., *A Novel Continuous Powder Aerosolizes (CPA) for Inhalative Administration of Highly concentrated Recombinant Surfactant Protein-C (rSP-C) Surfactant to Preterm Neonates*, JAMP, Vol. 26, No. 6, 2013, the administration of dry powdered aerosols into the ventilatory circuit and the respiratory tract which are both humid may result in a considerable unwanted deposition of powdered material, which may, finally, lead to a blockage of a tube or of an airway in the respiratory tract. These blockages may, thus, result in considerable obstructions in breathing for the patient up to suffocation. In particular small cross sections, such as the small cross sections which are, typically, used in respiratory support of preterm infants, comprise a high risk of suffocation. In addition, such unwanted deposition may render it difficult or even impossible to determine the exact dose of a substance to be administered which may have actually reached the target organ.

WO 2015/132172 A1 discloses a humidifier which is configured to humidify an aerosol. In particular by adjusting the temperature a thin liquid film is generated on surfaces of the previously dry particles. As result, dry particles which would otherwise be deposited on walls of the device or on the oral mucosa can simply be drained off by using this thin liquid film. Herein, the humidifier may be used in connection with an aerosolization device and the humidified aerosol may be provided to a patient who is either an actively breathing patient or a mechanically ventilated patient.

US 2014/216446 A1 discloses a device for providing a breathing gas stream, which contains a therapeutically active substance, for the mechanical respiration and/or mechanical breathing assistance of a patient. Herein, the device has at least one first line, through which a first gas stream flows during the operation of the device, and at least one second line, wherein the first line and the second line have a common section and are connected to one another by a water vapor-permeable membrane in the area of the common flow section. Further, a second gas stream to flow through the second line during the operation of the device is provided.

WO 2012/025496 A1 relates to aerosolized and humidified particles comprising a therapeutically active substance which can be obtained by suspending dry inhalable particles in a carrier gas, adding water vapor and causing condensation of water on the particles. Further, methods to generate these particles and an apparatus useful to carry out such methods are disclosed therein.

In addition, WO 2008/030592 A2, WO 2014/095858 A1, U.S. Pat. No. 5,031,612 A, and GB 2 465 358 A disclose methods and devices which contribute to a technological background to the present invention.

Problem to be Solved

However, even diligently humidifying the aerosol particles may not be sufficient of avoiding an effect that the humidified aerosol particles may be subject to a subsequent partial redrying, such as by an incidence of heat, especially of solar radiation.

It is therefore an objective of the present invention to provide a method and a device for administering a humidified aerosol to a patient interface which at least partially avoids this problem. Consequently, it would be desirable to engage a method and a device which would allow keeping the aerosol particles in a humidified state during their whole administration.

SUMMARY OF THE INVENTION

This problem is solved by a method, a device and a use thereof for administering a humidified aerosol to a patient interface having the features of the independent claims. Preferred embodiments, which might be implemented in isolated fashion or in any arbitrary combination, are subject matter of the dependent claims.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect, the present invention refers to a method for administering a humidified aerosol to a patient interface.

As used herein, the term "powdered aerosol" refers to an aerosolizable material that comprises particles of a powdered substance which are suspended in a gas phase, wherein the particles may, in particular, be or comprise particles of a pharmaceutical preparation, such as, for example, a lung surfactant. For converting the particles into this state, the aerosolizable material has been treated in an aerosolization device by a compressed carrier gas in order to entrain the particles into a gas stream. In this state, the particles of the dry material are, preferably, distributed across the entire volume of the carrier gas, in particular, in a uniform and finely dispersed form.

As further used herein, the term "humidified aerosol" refers to a previously dry powdered aerosol that comprised previously dry particles which has been treated in a manner to generate humidified particles. Herein, the humidified aerosol may exhibit a high degree of relative humidity, preferably at least 50% relative humidity, more preferred at least 130% relative humidity, in particular, of 100% relative humidity, for a temperature at which the present method may be applied. Preferably, this temperature may be close to a body temperature, such as between 30° C. and 42° C. As mentioned above, known and device methods exist, such as the method and the humidifier of WO 2015/132172 A1, which may be applied for generating a humidified aerosol.

As generally used, the term "relative humidity" refers to a relative amount of water vapor being present in a mixture of water vapor and the carrier gas, such as in the respiratory gases. Thus, the relative humidity of the mixture, which may, preferably, be expressed as a percent value, typically indicates a ratio of water vapor with respect to the saturation humidity for a given temperature. Herein, water vapor may condensate onto the surfaces of the aerosol particles at a relative humidity above 100% whereas water being bound at the surfaces of the aerosol particles may vaporize at a relative humidity below 100%.

Consequently, a dynamic equilibrium between water in form of vapor and water bound at the surfaces of the aerosol particles exists at 100% relative humidity, wherein, in practice, the dynamic equilibrium exists in a range around 100% relative humidity as known by the skilled person. Further, by feeding a cool humidified aerosol into the mixture an increase of the evaporation of water vapor from the surfaces of the aerosol particles may occur, thus, resulting in a redrying of the particles.

Further, the term "ventilatory circuit" refers to a device being configured for a ventilation of respiratory gases as provided by a ventilator to a patient and from the patient back to the ventilator, hereby excluding the respiratory tracks of the patient. As used herein, the term "patient" may, in particular, refer to a human being of any age, in particular, including preterm infants. Further, the term "ventilation" relates to a process of accomplishing a movement of the respiratory gases, in particular, via alternating steps of inhalation and exhalation. In contrast to normally breathing patients who are capable of performing the circulation without any additional aids, patients who are subject to mechanical ventilation, require the respiratory gases at least partially to be provided from the ventilator via the ventilatory circuit. As used herein, the term "patient interface" refers to a unit being configured for providing a connection between the ventilatory circuit and the respiratory track of the patient which is therefore, in general, located adjacent to the patient. For this purpose, the patient interface may be integrated into, or attached to, the ventilatory circuit, wherein the ventilatory circuit may, in general, comprise a ventilator and tubes adapted for guiding gases from the ventilator to a patient interface and back. In particular, a suitable mouthpiece, a breathing mask, a nasal cannula or a tracheal cannula may be part of the patient interface or attachable thereto. However, other arrangements of the patient interface may also be feasible.

As generally known, the respiratory gases may, in addition, act as a carrier gas that can, preferably, be enriched by the humidified aerosol, thus, resulting in a process which may be described by the phrase "administering the humidified aerosol". Herein, the term "administering" refers to a process of allowing a controlled application of the respiratory gases and the humidified aerosol comprised hereby, in particular, by providing a predefined amount of the pharmaceutical preparation as comprised by the humidified aerosol per time period. As used herein, the term "respiratory gases" refers to a gas mixture which comprises a composition being suitable for the ventilation of a patient, in particular, air or oxygen-enriched air.

Investigations with humidified aerosols have revealed that the humidified previously dry aerosol particles may be subject to a partial redrying, such as by an incidence of heat, especially of solar radiation. However, other reasons for causing a drying of the aerosol may also occur. In particular, the heat may cause an increase of temperature in the ventilatory circuit in a manner that the temperature of the completely humidified aerosol, which has been provided at 100% relative humidity, may increase. As described above, the humidified aerosol may gradually lose water at increasing temperatures, thus, leading to a successively drying of the aerosol. The administration of the successively more and more dried powdered aerosol may, thus, similar to the case of administration of a dry aerosol, result in a considerable amount of deposited powdered material, which may, finally, lead to a blockage of a tube or an airway in the respiratory tract. This result may, particularly, be due to the fact that deposited dry powder cannot rinse away. As already indicated above, these blockages may, thus, result in considerable obstructions in breathing up to suffocation of the patient.

Alternatively or in addition, even when a first flow of a 100% humidified aerosol and a second flow of 100% humidified carrier gas are separately guided until they are mixed into a mixture at a mixing chamber which may be located adjacent to the patient interface, a similar effect may be observable when the separately guided flows may exhibit a different temperature. In this case, it may rather be likely that the common temperature of the mixture in the mixing chamber may rise above a dew point of the mixture, thus, resulting in a loss of water of the surface of the particles. This effect may, especially, be dangerous in nasal prongs which are, typically, used in the respiratory support of preterm infants since they comprise particularly small cross sections, thus, leading to a high risk of suffocation of the infant.

As a result, when a gaseous flow which exhibits 100% relative humidity is cooled along a pathway, the relative humidity of this stream may always assume 100% along the pathway as long as vapor which has become redundant due to the decreasing temperature may be deposited on available surfaces. Further, when two of such flows, wherein the first flow may comprise the enriched carrier gas with the humidified aerosol and the second flow the respiratory gases, may be mixed, it can be particularly advantageous when the temperatures of the flows are the same at their arrival in the mixing chamber since 100% relative humidity is retained in this case. As a result, no redrying of the aerosol particles may occur. It is, thus, proposed to thermally balance the two flows prior to their mixing. In addition, a liquid flow comprising a thermally shielding against environmental heating or cooling and applying a constant temperature gradient along the gas pathways is applied in order to be able to also achieve the desired thermally balancing between the first flow and the second flow.

The method for administering a humidified aerosol to a patient interface, thus, comprises the following steps a) to f):
  a) providing and guiding a first gas flow comprising a humidified aerosol;
  b) providing and guiding a second gas flow comprising humidified respiratory gases;
  c) providing and guiding a liquid flow of a thermally balancing liquid;
  d) thermally balancing the first gas flow and the second gas flow by parallel guiding the first gas flow and the second gas flow, wherein the first gas flow and the second gas flow are guided in a manner that they are at least partially surrounded by the liquid flow of the thermally balancing liquid;
  e) mixing the first gas flow and the second gas flow, whereby enriched respiratory gases comprising the humidified aerosol are obtained; and
  f) administering the enriched respiratory gases comprising the humidified aerosol to the patient interface.

Herein, although the indicated steps may be performed in the given order, wherein, preferably, all of the indicated steps may be preformed at least partially concurrently. Further, additional method steps, whether described in this document or not, may be performed, too.

According to steps a) and b), each of the first gas flow comprising the humidified aerosol and of the second gas flow comprising the humidified respiratory gases are provided and guided, preferably separately provided and separately guided, wherein, according to step d), the first gas flow and the second gas flow are thermally balanced, particularly prior to step e), by parallel guiding the first gas flow and the second gas flow. In a particularly preferred embodiment in which the first gas flow comprising the humidified aerosol may exhibit a smaller flow volume compared to the second gas flow comprising the humidified respiratory gases, the second gas flow may be guided in a manner that it may at least partially, preferably fully in a lateral direction of the flow, surround the first gas flow. However, other arrangements may also be feasible.

According to step c), the thermal balancing of the first flow and of the second flow is supported by the liquid flow of the thermally balancing liquid which is separately provided and separately guided in a manner that it may at least partially, preferably fully in a lateral direction of the flow, surround both the first gas flow and the second gas flow. In particular, the liquid flow may be applied in form of a counter flow arrangement, thus, increasing an effectivity of the thermal balancing. Herein, the term "counter flow" refers to an arrangement in which the liquid flow may assume an opposite direction compared to the directions of the first flow and of the second flow. However, a parallel flow of the first gas flow, the second gas flow and the liquid flow may also be feasible. As used herein, the term "thermally balancing liquid" refers to a liquid substance which is, generally, adapted for being used as a support in achieving a thermal balance between to the first flow and of the second flow. In this regard, the liquid flow may be configured for shielding of the aerosol and the respiratory gases against heat ingress from the surrounding. Consequently, the liquid flow may comprise a liquid which may, preferably, exhibit a high heat capacity. For this purpose, the thermally balancing liquid may, preferably, be selected from one of water or an aqueous solution. However, other kinds of liquids, such as a non-aqueous liquid or a non-aqueous solution can also be used.

In a particularly preferred embodiment, the liquid flow of the thermally balancing liquid may be guided by applying a lower pressure in flow direction, such as by using a pumping unit which may be adapted for applying a lower pressure at the liquid flow, thus, being able to suck the thermally balancing liquid instead of pressing it. This arrangement may help avoiding that the thermally balancing liquid, i.e. the water or the aqueous solution, may intrude into the first gas and/or the second gas flow which is subject to be administered to the patient interface according to step f). As a consequence of this embodiment, a lower pressure may be generated in the liquid flow, thus, inhibiting an intrusion of the thermally balancing liquid into the ventilatory circuit which may, otherwise, result in a suffocation of the patient.

The liquid flow may, in particular, be configured for shielding both the first flow and the second flow from any ambient influence as far as possible, thus, allowing a considerably accurate setting of the common temperature of the mixture generated by the first flow and of the second flow. For this purpose, the first gas flow may be provided during step a) at a first temperature, wherein the second gas flow may be provided during step b) at a second temperature, whereas the first gas flow and the second gas flow are guided according to step d) in a manner that they can be mixed during to step e) at a common temperature. Herein, the common temperature used for the mixing of the first gas flow and of the second gas flow may, preferably, be both lower than the first temperature and the second temperature. In a particularly preferred embodiment, the common temperature may, additionally, be adjusted to a temperature, in particular within a range ±1° C., preferably of ±0.5° C., more preferred of ±0.3° C., that can be determined for a breath of the patient, such as by using a thermometer or a thermocouple. However, other methods for determination of the temperature may also be feasible. As a result of this accurately adjusted temperature, a redrying of the humidified aerosol during their mixing may practically be avoided, thus, additionally inhibiting a blockage of the patient interface. In addition, it may, particularly, be preferred when the first gas flow and the second gas flow may be mixed during step e) in a manner that the resulting mixture also comprises 100% relative humidity.

According to step f), the enriched respiratory gases comprising the humidified aerosol, preferably exhibiting 100% relative humidity, may, thus, be administered to the patient interface, hereby allowing the controlled application of the enriched respiratory gases which comprise the humidified aerosol, in particular, by providing the respiratory gases together with a predefined amount of the pharmaceutical preparation comprised by the humidified aerosol per time period, practically without any lasting deposition of re-dried aerosols in the device according to the present invention.

As further mentioned above, both the first gas flow and the second gas flow may be provided at 100% relative humidity during step a) or step b), respectively. For this purpose, a previously dry aerosol may be humidified prior to step a) while previously dry respiratory gases may be humidified prior to step b), in particular by applying a first humidifier for the dry aerosol and a second humidifier for the dry respiratory gases. As used herein, the term "dry" with respect to the dry aerosol and the dry respiratory gas may refer to a condition of the aerosol and of the respiratory gases comprising less than 100% relative humidity, thus, allowing them to incorporate more water vapor to be at least further humidified.

In a further aspect, the present invention refers to a device for administering a humidified aerosol to a patient interface. Accordingly, the device comprises:

- at least one first tube for receiving and guiding a first gas flow comprising a humidified aerosol;
- at least one second tube for receiving and guiding a second gas flow comprising humidified respiratory gases;
- at least one third tube for receiving and guiding a liquid flow comprising a thermally balancing liquid;

wherein the first tube, the second tube and the third tube are provided in a coaxial arrangement with respect to each other, wherein the third tube covers the first tube and the second tube; and

- at least one mixing chamber for receiving and mixing the first gas flow and the second gas flow and obtaining enriched respiratory gases comprising the humidified aerosol, the mixing chamber having at least one outlet for administering the enriched respiratory gases comprising the humidified aerosol.

As used herein, the term "tube" refers to a hollow, elongated object which is configured for receiving and guiding a flow of a gas and/or of a liquid. Herein, any one or each of the tubes as mentioned herein may be a rigid tube, such as a pipe, or, preferably, a semi-rigid or, more preferred, a flexible tube, such as a hose or a sleeve. In this manner, by using the flexible tube, the device according to the present invention could, advantageously, more easily be adjusted to the requirements of the patient. In order to allow a substantially constant liquid or gas flow through the tube, thereby reducing a risk of possible depositions, any one or each tube may, thus, comprise a substantially constant cross section along their length.

Further, each of the tubes may have an axis, wherein the axis of two or, preferably, of all three different tubes may coincide with respect to each other, thus, providing a triaxial arrangement of the first tube, the second tube and the third tube. Herein, the third tube may, preferably, cover the first tube and the second tube, in particular, in form of a jacket or a sheath covering both the first tube and the second tube. This kind of arrangement may, in particular, be advantageous, in order to achieve an effective cooling of both the first gas flow and the second gas flow inside their respective tubes. In a particularly preferred embodiment, in which the first tube configured for receiving and guiding the humidified aerosol may exhibit a smaller flow volume compared to the second tube configured for receiving and guiding the humidified respiratory gases, the first tube may be located inside the second tube, thus, allowing the second gas flow at least partially, preferably fully, surrounding the first gas flow. In this particularly preferred embodiment, it may be sufficient that the third tube may directly cover only the second tube since the second tube already covers the first tube being located inside the second tube. However, other arrangements may also be feasible, especially, when more than one first tube and/or more than one second tube and/or more than one third tube may be employed.

While the first tube is configured for receiving and guiding a first gas flow comprising a humidified aerosol, the second tube is configured for receiving and guiding a second gas flow comprising humidified respiratory gases. In a particular embodiment, the device may, thus, further comprise at least one first humidifier being configured for humidifying dry aerosol and at least one second humidifier being configured for humidifying dry respiratory gases. Herein, one or both of the humidifiers may be selected according to the disclosure of WO 2015/132172 A1. However, other arrangements and other kinds of humidifiers may also be feasible.

In a further preferred embodiment in which the third tube may comprise an inlet for receiving the thermally balancing liquid and an outlet for dispensing the thermally balancing liquid, the device may further comprise a pumping unit which may be configured for applying a lower pressure at the outlet of the third tube compared to the pressure at the inlet of the third tube, thus, allowing sucking the thermally balancing liquid through the third tube instead of pressing it into the third tube. As described above, this arrangement may help avoiding that the thermally balancing liquid, i.e. the water, the aqueous solution, the non-aqueous liquid, or the non-aqueous solution, may intrude into the first tube and/or the second tube. As a consequence of this embodiment, the lower pressure that may be generated in the liquid flow may, thus, inhibit an intrusion of the thermally balancing liquid into the ventilatory circuit which may, otherwise, result in a suffocation of the patient.

Herein, the mixing chamber may assume any possible form which may be suitable for receiving and mixing the first gas flow and the second gas flow and obtaining enriched respiratory gases comprising the humidified aerosol and which has at least one outlet for administering the enriched respiratory gases comprising the humidified aerosol. In a particularly preferred embodiment, the mixing chamber may be identical with the patient interface, wherein the outlet may be configured for administering the enriched respiratory gases comprising the humidified aerosol to the respiratory track of the patient or to an additional device that may be located between the patient interface and the respiratory track of the patient. In an alternative embodiment, the outlet of the mixing chamber may be configured for administering the enriched respiratory gases comprising the humidified aerosol to the patient interface or to an additional device that may be located between the outlet and the patient interface.

For further details with respect to the device reference may be made to the description of the method and of the exemplary embodiments elsewhere in this document.

In a further aspect, the present invention refers to a use of a device for administering a humidified aerosol to a patient interface in respiratory support of preterm infants. As already indicated above, small cross sections, such those which are typically used in respiratory support of preterm infants, may, especially, profit from the considerably reduced high risk of suffocation which can be achieved by the device according to the present invention.

Consequently, the method and the device according to the present invention may, thus, particularly allow avoiding the administration of dry or re-dried powdered aerosols. As a result, no unwanted deposition of powdered material which can, finally, lead to a blockage of a tube or, subsequently, of an airway in the respiratory tract may occur. Advantageously, no obstructions in breathing up to suffocation of the patient may be due to an absence of such a kind of deposition. Especially, small cross sections, such those which are typically used in respiratory support of preterm infants, may profit from the considerably reduced high risk of suffocation. The absence of such unwanted deposition may render it far easier to determine which exact dose of a substance to be administered may have actually reached the target organ.

In addition, the mixing of the first gas flow and the second gas flow, which may be provided at different temperatures, at a common temperature may, in particular, contribute to the mentioned advantages of the present invention. In addition, adjusting the common temperature to a temperature determined for a breath of a patient at least partially ventilated by the ventilatory circuit may result in an accurate temperature in the mixing chamber which may, additionally, provide support for avoiding the redrying of the humidified aerosol, thus, additionally inhibiting a blockage of the patient interface.

SHORT DESCRIPTION OF THE FIGURES

Further optional features and embodiments of the invention will be disclosed in more detail in the subsequent description of preferred embodiments, preferably in conjunction with the dependent claims. Therein, the respective optional features may be implemented in an isolated fashion as well as in any arbitrary feasible combination, as the skilled person will realize. It is emphasized that the scope of the invention may not be restricted by the preferred embodiments. The embodiments are schematically depicted in the Figures. Therein, identical reference numbers in these Figures refer to identical or functionally comparable elements.

In the Figures:

FIGS. 1A and 1B schematically illustrate a profile (FIG. 1A) and a cross section (FIG. 1B), respectively, of an exemplary device for administering a humidified aerosol to a patient interface according to the present invention;

FIGS. 2A and 2B schematically illustrate two different embodiments each comprising humidifiers attached to the exemplary device of FIGS. 1A and 1B; and FIGS. 3A and 3B show a comparison between images of cross sections of patient interfaces in form of nasal prongs inserted in a holder which are comparable to those that are, typically, used in respiratory support of preterm infants for administering a humidified aerosol to the patient interface without using the method and the device according to the present invention (FIG. 3A; state of the art) or by using the method and the exemplary device according to FIG. 1 or 2, respectively (FIG. 3B).

DETAILED DESCRIPTION OF THE EMBODIMENTS

FIG. 1A schematically shows a profile of an exemplary device 110 for administering a humidified aerosol 112 to a patient interface 114 according to the present invention. The device 110 may, in particular, be used for patients, including but not limited to preterm infants, who are subject to mechanical ventilation or to ventilatory support.

As depicted in FIG. 1A, the exemplary device 110 comprises a first tube 116 which is configured according to step a) for receiving and guiding a first gas flow 118 that comprises the humidified aerosol 112 to a mixing chamber 120. For this purpose, the first gas flow 118 may, preferably, be provided at a first inlet 122 of the first tube 116 at a first temperature $T_1$ and at 100% relative humidity.

As further shown in FIG. 1A, the exemplary device 110 further comprises a second tube 124 which is configured according to step b) for receiving and guiding a second gas flow 126 that comprises humidified respiratory gases 128 to the mixing chamber 120. Herein, the humidified respiratory gases 128 may comprise a composition which may be suitable for ventilation of the patient, in particular, air or oxygen-enriched air. For this purpose, the second gas flow 126 may, preferably, be provided at a second inlet 130 of the second tube 124 at a second temperature $T_2$ but also at 100% relative humidity.

As further illustrated in FIG. 1A, the exemplary device 110 further comprises a third tube 132 which is configured according to step c) for receiving and guiding a liquid flow 134 that comprises a thermally balancing liquid 136. Herein, the thermally balancing liquid 136 which refers to a liquid substance that is, generally, adapted for being used as a support in achieving a thermal balance between the first gas flow 118 and the second gas flow 126. For this purpose, the thermally balancing liquid 136 may, in particular, be selected from one of water or an aqueous solution. However, other kinds of liquid substances, such as a non-aqueous liquid or a non-aqueous solution, may also be feasible for this purpose.

Preferably, the third tube 132 may, as further schematically depicted in FIG. 1A, comprise an inlet 138 for receiving the thermally balancing liquid 136 and an outlet 140 for dispensing the thermally balancing liquid 136. In a particularly preferred embodiment, the device 110 may further comprise a pumping unit (not depicted here) which may be adapted for applying a pressure $p_2$ at the outlet 140 of the third tube 132 which may be lower compared to the pressure $p_1$ which may prevail at the inlet 138 of the third tube 132. In this manner the liquid flow 134 of the thermally balancing liquid 136 may be guided in a sucking motion through the third tube 132 instead of pressing it into the third tube 132. As a result, the arrangement as shown in FIG. 1A may, thus, help avoiding that the thermally balancing liquid 136 may intrude into the first tube 116 and/or into the second tube 124 and, eventually, into the patient interface 114 which may, otherwise, result in a suffocation of the patient.

As further schematically depicted in FIG. 1A, the liquid flow 134 may be applied in form of a counter flow arrangement in which the liquid flow 134 may assume an opposite direction compared to the directions of the first flow 118 and of the second flow 126, thus, allowing increasing an effectivity of the thermal balancing. However, a parallel flow of the first gas flow 118, the second gas flow 126 and the liquid flow 134 (not depicted here) may also be feasible.

Figure 2:
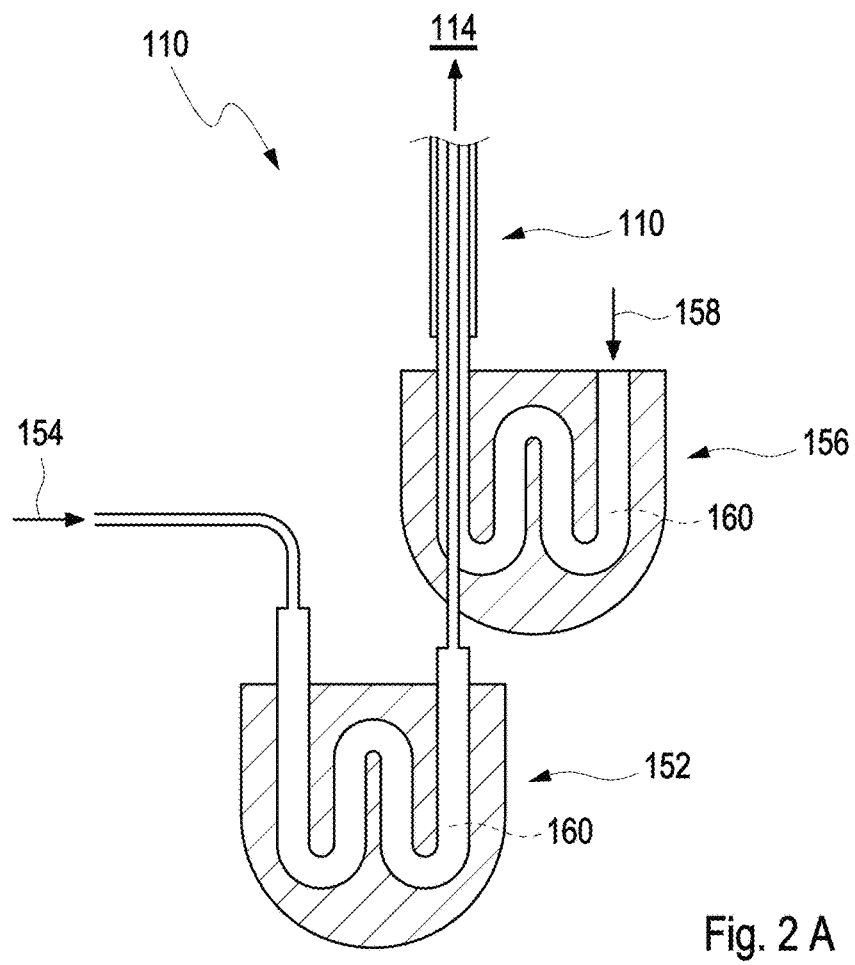
Figure 2:
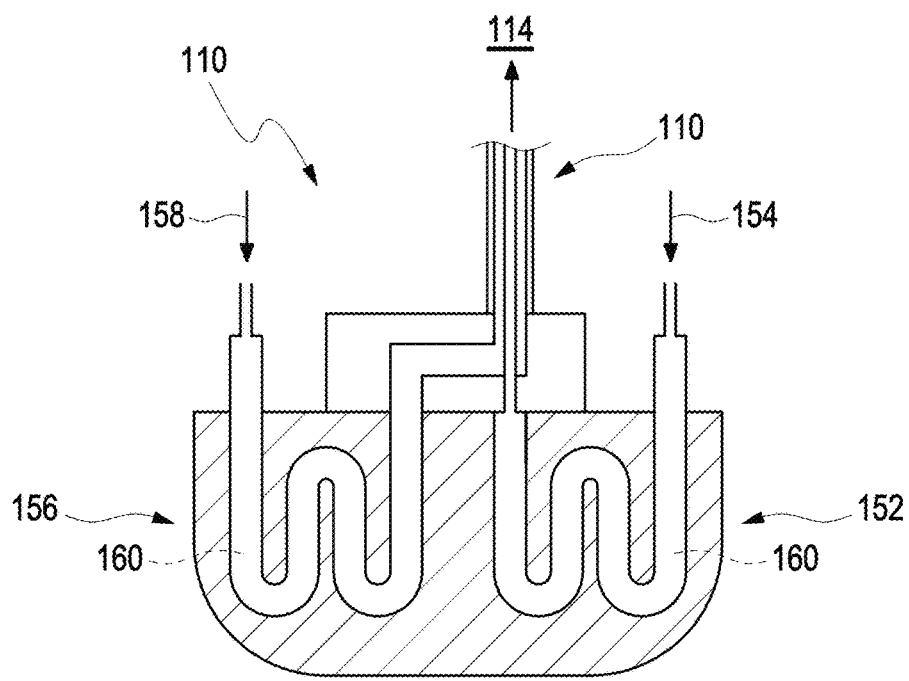

Any or, preferably, all of the first tube 116, the second tube 124 and the third tube 132 may be selected from a rigid tube, such as a pipe, or, preferably, from a semi-rigid or, more preferred, from a flexible tube, such as a hose or a sleeve. By using the flexible tube, the device 110 may, advantageously, more easily be adjustable to the requirements of the patient. In particular, any or, preferably, all of the first tube 116, the second tube 124 and the third tube 132 may comprise a substantially constant cross section along their length, especially, for allowing the first gas flow 118, the second gas flow 126 and/or liquid flow 134 to move in a substantially constant manner through the first tube 116, thereby reducing a risk of depositions, in particular of the aerosol 112 comprised by the first gas flow 118.

FIG. 1B schematically shows a cross section of the device 110 for administering the humidified aerosol to the patient interface 114 of the device 110 as illustrated in FIG. 1A. As depicted there, the first tube 116, the second tube 124 and the third tube 132 are provided in a coaxial arrangement with respect to each other, wherein the third tube 132 covers the first tube 116 and the second tube 124. In the exemplary embodiment as shown here; the first tube 116 has a first axis, the second tube 124 has a second axis, and the third tube 132 has a third axis, wherein the first axis, the second axis, and the third axis coincide with respect to each other, thus, resulting in a triaxial arrangement of the tubes 116, 124, 132. However, other arrangements may still be feasible.

Returning to FIG. 1A, it is illustrated there that, in accordance with the present invention, the second gas flow 126 is guided through the second tube 124 in a manner that it may at least partially surround the first gas flow 118 which is guided through the first tube 116. This arrangement may, preferably, be achieved by locating the first tube 116 inside the second tube 124, in particular, in a coaxial manner as shown in FIG. 1B. This embodiment may particularly be advantageous when the first tube 116 which is configured for receiving and guiding the humidified aerosol 112 may exhibit a smaller flow volume compared to the second tube 124 being configured for receiving and guiding the humidified respiratory gases 128.

The arrangement as illustrated in FIGS. 1A and 1B, thus, allows thermally balancing the first gas flow 118 and the second gas flow 126 according to step d) by parallel guiding the first gas flow 118 and the second gas flow 126. Herein, the first gas flow 118 and the second gas flow 126 may be guided in a manner that they are at least partially surrounded by the liquid flow 134 of the thermally balancing liquid 136. For this purpose, the third tube 132 may, preferably, have a form of a jacket or a sheath which may be designated for covering both the second tube 124 and, consequently, also the first tube 116 which is located inside the second tube 124 in the exemplary embodiment of FIGS. 1A and 1B. This kind of arrangement may, in particular, allow achieving an effective cooling of both the first gas flow 118 and the second gas flow 126 along their corresponding paths via the first tube 116 and the second tube 124 through which they are guided, respectively.

As further illustrated in FIG. 1A, the exemplary device 110 further comprises the mixing chamber 120 which, according to step e), is designed, on one hand, for receiving the first gas flow 118 from a first outlet 146 of the first tube 116 and the second gas flow 126 from a second outlet 148 of the second tube 124 and, on the other hand, for mixing the received first gas flow 118 and the received second gas flow

126, whereby enriched respiratory gases 142 which comprise the humidified aerosol 112, which may, preferably, be distributed across the entire volume of the respiratory gases 128 in a uniform and finely dispersed form, can be generated and provided via one or more outlets 150 according to step f).

As schematically depicted in FIG. 1A, the mixing chamber 120 may, in this particularly preferred embodiment, be identical with the patient interface 114 which, thus, comprises the outlets 150 for directly or indirectly administering the enriched respiratory gases 142. Herein, additional parts (not depicted here) may, in general, be introduced between the patient interface 114 and the respiratory tracks of the patient. In this particular embodiment, the patient interface 114 may, preferably, be comprise a further outlet 144, the further outlet 144 being configured for outputting exhaled gases as received from the patient.

In an alternative embodiment (not depicted here), the patient interface 114 may be attached in form of a separate unit to the outlets 150 of the mixing chamber 120. Also here, additional parts may, in general, be introduced between the mixing chamber 120 and the patient interface 114 and/or between the patient interface 114 and the respiratory tracks of the patient.

Considering that the first gas flow 118 assumes a third temperature $T_3$ at the first outlet 146 of the first tube 116 and the second gas flow 126 assumes a fourth temperature $T_4$ at the second outlet 148 of the second tube 124, the first gas flow 118 and the second gas flow 126 are mixed, preferably, in the mixing chamber 120 at a common temperature $T_c$. In a particularly preferred embodiment, the common temperature $T_c$ may equal both the third temperature $T_3$ and the fourth temperature $T_4$ but, due to cooling of both the first gas flow 118 and the second gas flow 126 along their respective tubes 116, 124, the common temperature $T_c$ may be lower than both the first temperature $T_1$ at the first inlet 12 of the first tube 116 and the second temperature $T_2$ at the second inlet 130 of the second tube 124.

In addition to the adjustment of the temperatures as described herein, the first gas flow 118 and the second gas flow 126 may, most preferred, be mixed in accordance with step e) at 100% relative humidity of all participating gas glows 118, 126. In order to arrive at this particularly preferred embodiment, the thermally balancing of both the first gas flow 118 and the second gas flow 126 according to step d) may be applied in the manner that the humidity and the common temperature $T_c$ in the mixing chamber 120 may assume the mentioned values.

As indicated above, this particularly preferred embodiment may ensure that practically no accumulation of powdered material may occur, thus, avoiding a blockage of a tube or of an airway in the respiratory tract. In order to further improve this advantage of the present invention, the thermally balancing of both the first gas flow 118 and the second gas flow 126 according to step d) can, additionally, be applied in a manner that the common temperature $T_c$ may be adjusted to a breath temperature $T_b$, wherein the breath temperature $T_b$ may be determined for a breath of a patient who is at least partially ventilated via the patient interface 114. In this regard, a thermometer or a thermocouple may be used for determining the breath temperature $T_b$. In this further improved embodiment any differences between the temperature of the breath of the actually ventilated patient and the temperature of the flow of the enriched respiratory gases 142 may disappear, thus, further contributing to avoiding a deposition in the patient interface 114.

As illustrated in FIGS. 2A and 2B, the exemplary device 110 may further comprise a first humidifier 152 configured to humidify a dry aerosol 154 and a second humidifier 156 configured to humidify dry respiratory gases 158. As already mentioned above, the term "dry" with respect to the dry aerosol 154 and the dry respiratory gases 158 refers to a condition of the aerosol and the respiratory gases which may comprise less than 100% relative humidity, thus, allowing the aerosol and the respiratory gases to be at least further humidified. Preferably, the dry aerosol 154 may be humidified prior to step a) and, subsequently, be guided as the humidified aerosol 112 to the first inlet 122 of the first tube 116 as shown in FIG. 1A. Similarly, the respiratory gases 158 may, preferably, be humidified prior to step b) and, subsequently, be guided as the humidified respiratory gases 128 to the second inlet 130 of the second tube 124 as further shown in FIG. 1A.

In the particular embodiments as depicted in FIGS. 2A and 2B, both the first humidifier 152 and the second humidifier 156 have been chosen in an arrangement as proposed in WO 2015/132172 A1. Accordingly, the humidifiers 152, 156 may each have a water compartment 160 comprising water which may be designated for humidifying the dry aerosol 154 or the dry respiratory gases 158, respectively. For further details, reference may be made to WO 2015/132172 A1, which is incorporated here by reference. However, other kinds of humidifiers and alternative arrangements may also be feasible.

Figure 3:
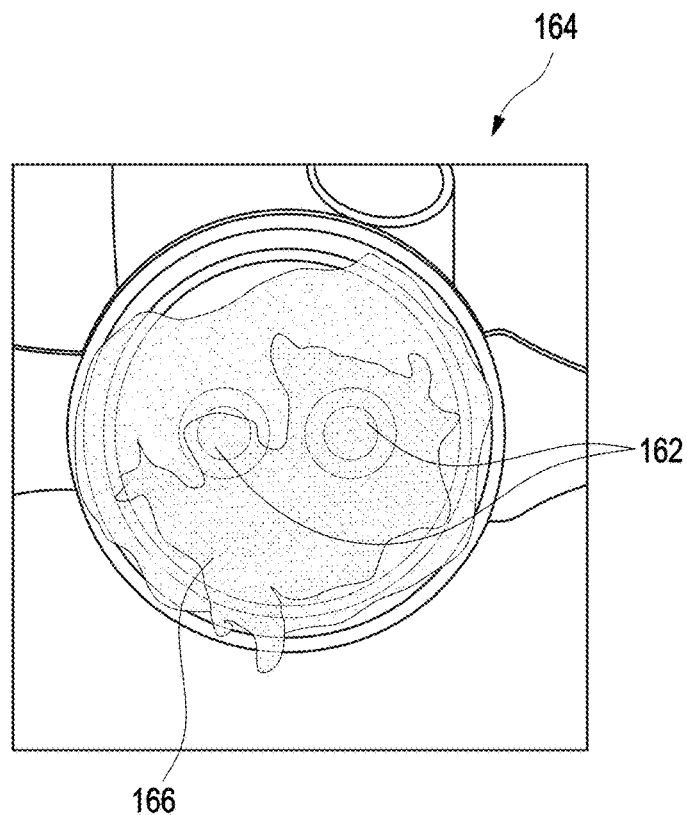
Figure 3:
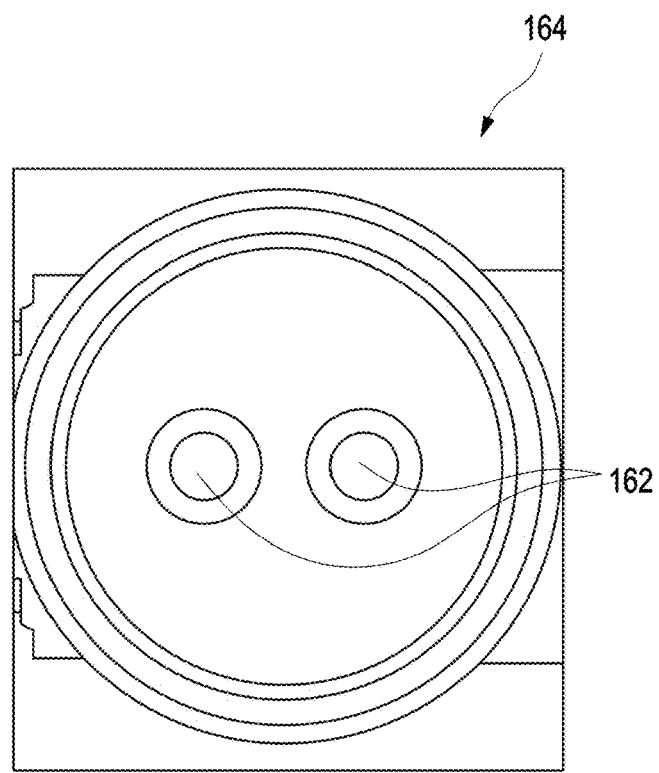

FIGS. 3A and 3B provide a comparison between cross sections of airways 162 comprised by a nasal prong 164 which is designed for being used as the patient interface 114 in respiratory support of preterm infants.

As shown in FIG. 3A, administering the humidified aerosol 112 to the patient interface 114 of the infant in accordance with the state of the art without application of the method and the device 110 according to the present invention, a considerable degree of unwanted powdered material deposition 166 may lead to a blockage of the airways 162 of the nasal prong 164. As illustrated here, this effect may, especially, be dangerous since it may lead to a high risk of suffocation of the infant.

In contrast hereto, practically no depositions can be observed when the dry aerosol 154 is humidified by applying the method and the device 110 for administering the humidified aerosol 112 to the patient interface 114 of the infant according to the present invention. Consequently, the method and the device 110 according to the present invention can effectively be applied even in this sophisticated case in order to avoid an at least partial redrying of the humidified aerosol 112 on its path to the patient interface 114.

LIST OF REFERENCE NUMBERS 110 device
112 humidified aerosol
114 patient interface
116 first tube
118 first gas flow
120 mixing chamber
122 first inlet
124 second tube
126 second gas flow
128 humidified respiratory gases
130 second inlet
132 third tube
134 liquid flow
136 thermally balancing liquid
138 inlet
140 outlet
142 enriched respiratory gases
144 further outlet
146 first outlet
148 second outlet
150 outlets
152 first humidifier
154 dry aerosol
156 second humidifier
158 dry respiratory gases
160 water compartment
162 airway
164 nasal prong
166 deposition

What is claimed is:

1. A method for administering a humidified aerosol to a patient interface, comprising the following steps:
    a) providing and guiding a first gas flow comprising the humidified aerosol;
    b) providing and guiding a second gas flow comprising humidified respiratory gases;
    c) providing and guiding a liquid flow of a thermally balancing liquid;
    d) thermally balancing the first gas flow and the second gas flow by parallel guiding the first gas flow and the second gas flow, wherein the first gas flow and the second gas flow are guided in a manner that they are at least partially surrounded by the liquid flow of the thermally balancing liquid;
    e) mixing the first gas flow and the second gas flow, whereby enriched respiratory gases comprising the humidified aerosol are obtained; and
    f) administering the enriched respiratory gases comprising the humidified aerosol to the patient interface.

2. The method of claim 1, wherein the second gas flow is guided in a manner that it at least partially surrounds the first gas flow.

3. The method of claim 1, wherein the first gas flow is provided pursuant to step a) at a first temperature, wherein the second gas flow is provided pursuant to step b) at a second temperature, wherein the first gas flow and the second gas flow are mixed pursuant to step e) at a common temperature, wherein the common temperature is lower than the first temperature and the second temperature.

4. The method of claim 3, wherein the common temperature is adjusted to a temperature determined for a breath of a patient at least partially ventilated by the ventilatory circuit.

5. The method of claim 1, wherein the first gas flow is provided pursuant to step a) at 100% relative humidity, wherein the second gas flow is provided pursuant to step b) at 100% relative humidity, and wherein the first gas flow and the second gas flow are mixed pursuant to step e) at 100% relative humidity.

6. The method of claim 1, wherein the liquid flow of the thermally balancing liquid is guided by applying a lower pressure in a flow direction.

7. The method of claim 1, wherein the thermally balancing liquid is selected from one of water, an aqueous solution, a non-aqueous liquid, or a non-aqueous solution.

8. The method of claim 1, wherein dry aerosol is humidified prior to step a) and wherein dry respiratory gases are humidified prior to step b).

9. The method of claim 1, wherein the humidified aerosol is administered in respiratory support of preterm infants.

10. A device for administering a humidified aerosol to a patient interface, comprising:
- at least one first tube for receiving and guiding a first gas flow comprising the humidified aerosol;
- at least one second tube for receiving and guiding a second gas flow comprising humidified respiratory gases;
- at least one third tube for receiving and guiding a liquid flow comprising a thermally balancing liquid;
- wherein the first tube, the second tube and the third tube are provided in a coaxial arrangement with respect to each other, wherein the third tube covers the first tube and the second tube; and
- at least one mixing chamber for receiving and mixing the first gas flow and the second gas flow and obtaining enriched respiratory gases comprising the humidified aerosol, the mixing chamber having at least one outlet for administering the enriched respiratory gases comprising the humidified aerosol.

11. The device of claim 10, wherein the first tube is located inside the second tube.

12. The device of claim 10, wherein the third tube forms a jacket directly or indirectly covering the first tube and the second tube.

13. The device of claim 10, wherein the first tube has a first central axis, the second tube has a second central axis, and the third tube has a third central axis, wherein the first central axis, the second central axis, and the third central axis coincide with respect to each other.

14. The device of claim 10, wherein the third tube comprises at least one inlet for receiving the thermally balancing liquid and at least one outlet for dispensing the thermally balancing liquid, wherein the device further comprises a pump being designed for applying a lower pressure at the outlet compared to the pressure at the inlet.

15. The device of claim 10, wherein at least one of the first tube, the second tube and the third tube is a flexible tube.

16. The device of claim 10, wherein at least one of the first tube, the second tube and the third tube comprises a constant cross section along their length.

17. The device of claim 10, further comprising at least one first humidifier configured to humidify dry aerosol and at least one second humidifier configured to humidify dry respiratory gases.

\* \* \* \* \*